US010808265B2

(12) United States Patent
Higashide et al.

(10) Patent No.: US 10,808,265 B2
(45) Date of Patent: Oct. 20, 2020

(54) MICROBES AND METHODS FOR IMPROVED CONVERSION OF A FEEDSTOCK

(71) Applicant: c/o NantBio, Inc., Culver City, CA (US)

(72) Inventors: Wendy M. Higashide, Los Angeles, CA (US); Xiaoqian Li, Los Angeles, CA (US); Lars Erik Ulf Rohlin, Los Angeles, CA (US)

(73) Assignee: NANTBIO, INC., Culver City, CA (US)

( * ) Notice: Subject to any disclaimer, the term of this patent is extended or adjusted under 35 U.S.C. 154(b) by 0 days.

(21) Appl. No.: 16/580,906

(22) Filed: Sep. 24, 2019

(65) Prior Publication Data

US 2020/0095617 A1 Mar. 26, 2020

Related U.S. Application Data

(60) Provisional application No. 62/736,787, filed on Sep. 26, 2018.

(51) Int. Cl.
| | | |
|---|---|---|
| *C12N 1/20* | (2006.01) | |
| *C12P 7/24* | (2006.01) | |
| *C12N 9/92* | (2006.01) | |
| *C12P 7/16* | (2006.01) | |
| *C12N 9/88* | (2006.01) | |
| *C12P 7/06* | (2006.01) | |

(52) U.S. Cl.
CPC .................. *C12P 7/24* (2013.01); *C12N 9/88* (2013.01); *C12N 9/92* (2013.01); *C12P 7/06* (2013.01); *C12P 7/16* (2013.01); *C12Y 401/02022* (2013.01); *C12Y 503/01005* (2013.01)

(58) Field of Classification Search
CPC .......................... C12N 9/92; C12Y 401/02009
USPC ................................ 435/147, 252.3
See application file for complete search history.

(56) References Cited

U.S. PATENT DOCUMENTS

| 7,851,188 B2 | 12/2010 | Donaldson et al. |
| 7,993,889 B1 | 8/2011 | Donaldson et al. |
| 8,048,666 B1 | 11/2011 | Green et al. |
| 8,097,439 B2 | 1/2012 | Alibhai et al. |
| 9,708,631 B2 | 7/2017 | Higashide et al. |
| 2009/0081746 A1 | 3/2009 | Liao et al. |
| 2011/0201083 A1 | 8/2011 | Liao et al. |

FOREIGN PATENT DOCUMENTS

| WO | 94/06924 A1 | 3/1994 |
| WO | 2009/086423 A2 | 7/2009 |
| WO | 2009/149240 A1 | 12/2009 |
| WO | 2010/062597 A1 | 6/2010 |
| WO | 2010/075504 A2 | 7/2010 |

OTHER PUBLICATIONS

Liu et al. J. Bacteriol. Oct. 2012 vol. 194 No. 19, pp. 5413-5422 (Year: 2012).*
Kim et al., "Simultaneous utilization of glucose and xylose via novel mechanisms in engineered *Escherichia coli*", 2015, Metabolic Engineering, vol. 30, pp. 141-148.
Utrilla et al., "Engineering and adaptive evolution of *Escherichia coli* for D-lactate fermentation reveals GatC as a xylose transporter", 2012, Metabolic Engineering, vol. 14, pp. 469-476.
Liu et al., "Phosphoketolase Pathway for Xylose Catabolism in Clostridium acetobutylicum Revealed by 13C Metabolic Flux Analysis", 2012, Journal of Bacteriology, vol. 194(19), pp. 5413-5422.

* cited by examiner

*Primary Examiner* — Tekchand Saidha
(74) *Attorney, Agent, or Firm* — Lucas & Mercanti, LLP

(57) ABSTRACT

Genetically engineered cells and methods are presented that enhance the consumption of xylose in a medium comprising a mix of five- and six-carbon sugars. Method of using these microbes to enhance xylose utilization and methods of making value products using these microbes are also disclosed herein.

16 Claims, 7 Drawing Sheets

Specification includes a Sequence Listing.

Plasmid Expression (w/IPTG added):
PLlacO1-*alsSilvCD* = pSA69
PLlacO1-*kivd* = pEB5
Chromosome Integration:
*adhE*:: PCP25-*alsSilvCD*
*yjgB*:: PCP25-*kivd*

MICROBES AND METHODS FOR IMPROVED CONVERSION OF A FEEDSTOCK

CROSS REFERENCE TO RELATED APPLICATIONS

This application claims the benefit of priority from U.S. provisional patent application Ser. No. 62/736,787 filed on Sep. 26, 2018, the contents of which are hereby incorporated by reference.

REFERENCE TO A SEQUENCE LISTING

This application contains references to amino acid sequences and/or nucleic acid sequences which have been submitted concurrently herewith as the sequence listing text file. The aforementioned sequence listing is hereby incorporated by reference in its entirety pursuant to 37 C.F.R. § 1.821(e).

The sequence listing includes the following sequences:
SEQ ID NO:1: Phosphoketolase derived from *Clostridium acetobutylicum*.
SEQ ID NO:2: Phosphoketolase derived from *Lactobacillus plantarum*.
SEQ ID NO:3: Nucleic acid encoding phosphoketolase derived from *Clostridium acetobutylicum*.
SEQ ID NO:4: Nucleic acid encoding phosphoketolase derived from *Lactobacillus plantaru*.
SEQ ID NO:5: D-xylose transport system subunit xylF.
SEQ ID NO:6: D-xylose transport system subunit xylG.
SEQ ID NO:7: D-xylose transport system subunit xylH.
SEQ ID NO:8: Nucleic acid encoding D-xylose transport system subunit xylF.
SEQ ID NO:9: Nucleic acid encoding D-xylose transport system subunit xylG.
SEQ ID NO:10: Nucleic acid encoding D-xylose transport system subunit xylH.

Field of the Invention

The field of the invention relates to genetically modified microbes and methods for the simultaneous utilization of xylose and glucose in a fermentation process

Background

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Microbes can synthesize oxo-chemicals such as biofuels and industrial feedstocks using metabolically engineered microbial cells. For example, microbial ethanol production from carbohydrates is described in WO 94/06924. Ethanol production from CO2 is reported in U.S. Pat. No. 8,048,666. Short-chain alcohol production from 2-keto acids using metabolically engineered cells is described in US 2009/0081746. U.S. Pat. Nos. 7,851,188 and 7,993,889, and WO 2009/086423, WO 2009/149240, WO 2010/062597, and WO 2010/075504 all report isobutanol production from metabolically engineered cells. $C_{5-8}$ alcohol production from 2-keto acids using metabolically engineered cells is described in US 2011/0201083. U.S. Pat. No. 8,097,439 reports fatty aldehyde production from various carbon sources. U.S. Pat. No. 9,708,631 describes microbial synthesis of isobutyraldehyde.

Kim et al. (2015) *Metabolic Engineering* 30:141-48 describe an engineered *E. coli* capable expressing xylose isomerase (xylA) and xylulose kinase (xylB). This modified *E. coli* can use glucose and xylose simultaneously.

Utrilla et al. (2012) *Metabolic Engineering* 14:469-476 report that deletion of the xylFGH transporter system enhances lactate production from a xylose feedstock without significantly impacting its specific xylose consumption rate.

Liu et al. (2012) *J. Bacteriol.* 194(19):5413-22 report cloning a xylose/fructose phosphoketolase (xfp) from *Clostridium acetobutylicum*. Liu et al. report (pg. 5421) a "strongly decreased xylose fermentation rate in the phosphoketolase-overexpressing [*E. coli*] strain during the solventogenic phase."

Further improvements in the efficiency of producing value products from the glucose and xylose sugars obtained from the breakdown hydrolysis of lignocellulosic biomass are still needed. There is also still a need for methods and compositions that permit efficient carbon fixation by autotrophic organisms under conditions that also permit efficient production of value added materials without imposing undue metabolic burden and additional catalytic activities onto a cell. Moreover, there is also a need to provide metabolically engineered cells that can produce value products at a high rate in a feedstock comprising both 5-carbon and 6-carbon sugars.

SUMMARY

Various genetically engineered cells, systems, and methods of production of various value products from mixed sugar feedstocks are disclosed herein. In certain embodiments, genetically modified microbes are disclosed herein overexpressing (e.g., constitutively expressing) xyloseisomerase (xylA). In certain embodiments, these xylA expressing organisms (e.g., *E. coli*) also express a d-xylose ABC transporter (xylFGH) and/or fructose-6-phosphate phosphoketolase (xfp). In certain embodiments, the microorganism expressing xylFGH and/or xfp also overexpresses a xylulokinase (xylB).

In certain embodiments, these modified microbes can be used in methods of fermentation to produce value products from feedstocks containing both glucose and xylose. For example, the microbes disclosed herein can be used to ferment feedstocks derived from biological waste (e.g., corn stover) in which glucose and xylose are both present. In certain embodiments, these methods achieve improved xylose usage in the presence of glucose than is achieved with prior art microbes.

Various objects, features, aspects and advantages of the inventive subject matter will become more apparent from the following detailed description of preferred embodiments, along with the accompanying drawing figures.

DETAILED DESCRIPTION

Figure 1:
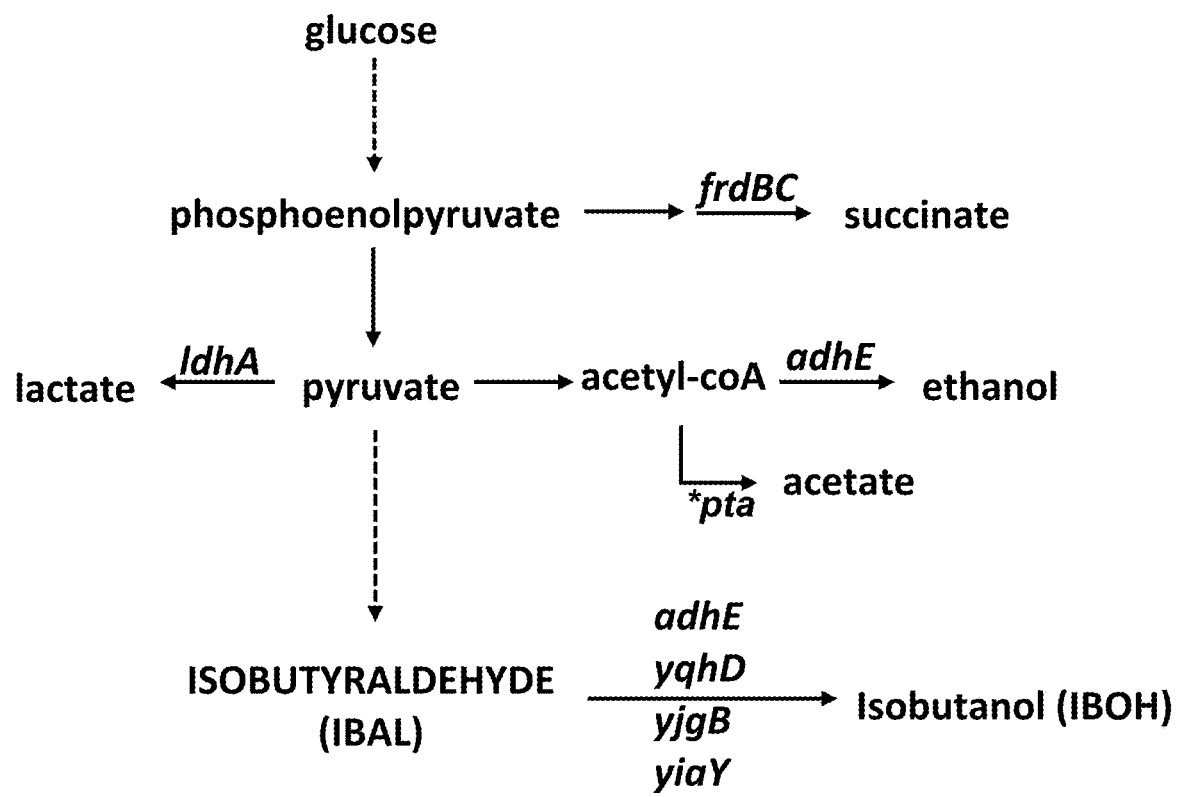
FIG. 1 lists a variety of genetic modifications and their relevance to the biosynthesis of isobutyraldehyde from pyruvate.

In interpreting both the specification and the claims, all terms should be interpreted in the broadest possible manner consistent with the context. The following terms are defined. Unless otherwise indicated, the terms listed below will be used and are intended to be defined as stated, unless otherwise indicated. Definitions for other terms can occur throughout the specification.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. The term, "consisting essentially of" should be interpreted as exclusive in scope, but allowing for non-essential elements, components or steps that are not expressly referenced, to be included.

As also used in the description herein and throughout the claims that follow, the meaning of "a," "an," and "the" includes plural reference unless the context clearly dictates otherwise. Likewise, the meaning of "in" includes "in" and "on" unless the context clearly dictates otherwise. Where the specification and claims refer to at least one of something selected from the group consisting of A, B, C . . . and N, the text should be interpreted as requiring only one element from the group (i.e., not limited to "A+N," or "B+N," etc.), but extending to any variety of combinations within the specified set (e.g., "A," or "A+B+N," or "B+N," etc.).

The term "native" refers to nucleic acid sequences or amino acid sequences as they naturally occur in the host. The term "non-native" is used herein to refer to nucleic acid sequences or amino acid sequences that do not occur naturally in the host. "Non-native" genes include genes endogenous to the host microbe operably linked to one or more heterologous regulatory sequences that have been inserted into the host genome.

The recitation of ranges of values herein is merely intended to serve as a shorthand method of referring individually to each separate value falling within the range. Unless otherwise indicated herein, each individual value is incorporated into the specification as if it were individually recited herein.

As used herein, "overexpression" of a gene means expression of that gene to form a gene product in an amount such that the amount is greater than zero or in an amount that is greater than an amount that would otherwise be already present in the cell without the overexpression.

Glucose and xylose are the two most common sugars in lignocellulosic carbon sources (Kim et al. 2015). However, most microbes downregulate xylose fermentation enzymes in the presence of glucose, such that xylose fermentation is only activated once glucose is consumed. Kim et al. 2015 find that if a constitutive promoter is inserted upstream of the xylAB operon, the resulting microbe will utilize xylose in the presence of glucose.

It is herein disclosed that the increased utilization of xylose in the presence of glucose that is achieved by overexpressing xylA can be further enhanced by overexpressing xylFGH and/or xfp. These findings are surprising because Utrilla et al. 2012 report that xylFGH does not significantly impact specific xylose consumption rate, and Liu et al. 2012 report that overexpressing xfp decreases xylose fermentation. In other words, while the prior art suggests that overexpressing xfp or xylFGH should have no effect on xylose metabolism in a mixed glucose/xylose environment—or might even inhibit xylose metabolism—the present application reveals that xfp and xylFGH each actually improve xylose utilization from a mixed glucose/xylose feedstock in the context of a host cell overexpressing xylA.

Engineered microbes are disclosed herein that eliminate the production of unwanted byproducts during the fermentation process, and that produce an aldehyde and/or alcohol product when provided with a carbon source comprising glucose and xylose sugars. Preferably, the carbon source is biomass, or is derived from a biomass source. These engineered microbes express (e.g., constitutively overexpress) a non-native xylose isomerase (xylA) gene and (optionally) a non-native xylulose kinase (xylB) gene. In certain embodiments, the engineered microbes also express (e.g., constitutively overexpress) a non-native fructose-6-phosphate phosphoketolase (xfp gene) and/or one or more non-native components of a d-xylose ATP binding cassette (ABC) transporter (xylFGH genes) during the fermentation process.

Expression of the genes listed above drives the engineered microbes to metabolize xylose even when glucose is present in the carbon source. In certain embodiments, the engineered microbe will have one or both of a non-native xfp or a non-native xylF, xylG, and/or xylH gene. The non-native xfp gene can be expressed transiently or stably. In certain embodiments, the xfp is encoded on a vector, such as a plasmid vector. In other embodiments, the xfp is encoded on the chromosome. Additionally or alternatively, the non-native xylF, xylG, and/or xylH genes can be expressed can be expressed transiently or stably. In certain embodiments, xylFGH is encoded on a vector, such as a plasmid vector. In other embodiments, xylFGH is encoded on the chromosome.

The engineered microbe is prepared from any one of a variety of microbes—including various bacteria, cyanobacteria, and fungi—that are then modified to enhance the simultaneous utilization of glucose and xylose. For example, the microbe in certain embodiments can be a prokaryote, such as a prokaryote belonging the genus of *Escherichia, Bacillus, Corynebacterium, Alcaligenus, Zymomonas, Clostridium, Lactobacillus, Synechococcus*, or *Synechocystis*, among other microorganisms. Alternatively, the engineered microbe can be a eukaryote, such as a eukaryote belonging to the genus of *Saccharomyces, Pichia, Candida*, or *Aspergillus*, among other organisms. In particularly preferred embodiments, the microbe is *Escherichia coli, Bacillus subtilis, Synechococcus elongatus, Ralstonia eutropha*, or *Saccharomyces cerevisice*. As described below, BW25113 (a derivative of *E. coli* K-12) was utilized as an exemplary starting organism.

The engineered microbe may be prepared using any method known in the art. It will be understood that modifications may include insertion or deletion of one or more genes as deemed necessary to increase or decrease activity of a particular enzymatic pathway. In some embodiments, a mutant microbe may also be used in the methods of the present invention, and may be further modified by recombinant methods as desired. Thus, suitable modifications will include random mutagenesis to produce deficient expression patterns, extrachromosomal (typically plasmids or phagemid) nucleic acids with suitable control elements to produce controlled overexpression of one or more enzymes, genomic insertions with suitable control elements to produce controlled overexpression of one or more enzymes, etc.

In certain embodiments of the engineered microbe, the production of undesirable end products is minimized or avoided by disabling genes in the pathways to the undesirable products. As described below for *E. coli*, genes that can be disabled by selective deletions include, for example, one or more of the ldhA, frdBC, adhE, yqhD, yjgB, yiaY and pta genes, to name but a few such genes.

Thus, in one embodiment, the microbe is engineered to constitutively express xylA (xylose isomerase; EC 5.3.1.5) and xylB (xylulose kinase; EC 2.7.1.17), allowing the microbes to metabolize xylose even when there is glucose present in the environment. In a further embodiment, the microbe also expresses the xfp gene (xylulose/fructose phosphoketolase) in the xylAB overexpressing background. In a still further embodiment, the microbe also expresses the xylFGH genes (d-xylose ABC transporter) in the xylAB overexpressing background.

Xylose/fructose phosphoketolase utilizes xylulose-5-phosphate or fructose-6-phosphate as a substrate and generates acetylphosphate—an acetyl-CoA precursor—and erythrose-4-phosphate as a product. Phosphoketolase, EC 4.1.2.9—in particular fructose-6-phosphate phosphoketolase (xfp, EC 4.1.2.22)—can be found in numerous sources, and cloning and stable or transient expression will follow generally well-known laboratory protocols using appropriate vectors. For example, phosphoketolase is known from *Lactobacillus plantarum* (see e.g., Jeong et al. (2007) *J Microbiol Biotechnol.* 17(5):822-29), *Bifidobacterium breve* (see e.g., (2014) *BMC Genomics.* 15:170), *Bifidobacterium adolescentis* (see e.g., (2009) *Appl Microbiol Biotechnol.* 83(6):1115-26), *Acetobacter xylinum* (see e.g., (1958) *J. Biol. Chem.* 233(6):1283-88), *Bifidobacterium longum* (see e.g., (2001) *Lett Appl Microbiol.* 32(4):235-39), etc. In certain embodiments, the phosphoketolase can have at least about 50% (for example, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%) identity to SEQ ID NO:1 or SEQ ID NO:2.

Likewise, phosphoribulokinase EC 2.7.1.19 is well known and can be cloned from numerous sources, and cloning and stable or transient expression will follow generally well-known laboratory protocols using appropriate vectors. For example, phosphoribulokinase can be cloned from *Arabidopsis thaliana* (see e.g., (2005) *J Exp Bot.* 56(409):73-80), *Rhodobacter sphaeroides* (see e.g., (2006) *Protein Sci.* 15(4):837-42), etc.

The xylose isomerase (xylA), xylulose kinase (xylB), and d-xylose ABC transporter (xylFGH) genes are all native to *E. coli*, as well as a variety of other bacterial species. When necessary, these genes can be cloned from *E. coli* using ordinary techniques known to the art. Alternative, when working with *E. coli* as the host organism, these genes can be made non-native by replacing the promoters driving the xyl genes with one or more heterologous promoters. Additionally or alternatively, the xyl genes can be cloned from other known organisms beyond those of the *Escherichia* genus. In certain embodiments, the xylFGH genes can encode proteins having at least about 50% (for example, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%) sequence identity to SEQ ID NOs:5, 6, & 7.

In certain embodiments, an engineered microbe can be optimized for isobutyraldehyde production by ablating genes (e.g., ldhA, frdBC, etc.) that would divert isobutyraldehyde precursors into non-desired pathways as discussed above. Additionally or alternatively, the engineered microbes can overexpresses the xylFGH gene (xylose transporter) in a xylAB overexpressing background. Additionally or alternatively, the engineered microbes can overexpress xfp in a xylAB overexpression background, and/or an xylFGH overexpressing background.

Where it is considered desirable, the genes to be overexpressed in the microbes described herein can be codon-optimized for their host organisms. Codon optimization is known in the art for a variety of host organisms, including *E. coli* and *S. cerevisice*. Puigbò et al. (2007) *Nuc. Acids Res.* 35(S2):W126-31.

Methods of making and using these engineered microbes are also provided. When the carbon source is a lignocellulose, the lignocellulose must first be treated or processed (saccharified) to release sugars such as glucose and xylose that can be readily fermented. The lignocellulose can be saccharified by any known method, including heating under acidic or alkaline conditions, and/or subjected to enzymatic degradation or pre-treatment with microbes engineered to release enzymes promoting the breakup of cellulose and/or lignins to simple sugars. The saccharification process will produce a biomass hydrolysate enriched in fermentable sugars. Exemplary saccharification methods are described, for instance, in U.S. Pat. Nos. 10,036,049; 10,036,049; 10,023,881; 9,988,658; 9,970,039; and U.S. Pat. No. 9,938,552.

As described in U.S. Pat. No. 7,803,623, biomass saccharification produces sugars in a biomass hydrolysate that may typically include a mixture of xylose with glucose, fructose, sucrose, galactose, mannose, and/or arabinose. The ratio of different sugars may vary in the mixture, with xylose typically at least about 10%, or in a ratio ranging from about 10% to about ≥40% of the total amount of sugars in the biomass hydrolysate.

Additionally or alternatively, the engineered microbe as described herein can be incubated in a defined medium composition comprising fermentable sugars. The fermentation can be conducted at any suitable temperature and pressure conditions known in the art (e.g., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C. or higher). Fermentation can be allowed to proceed for as long as is required to consume all fermentable sugars, or for a fixed amount of time (e.g., 1 hr., 2 hrs., 5 hrs., 10 hrs., 15 hrs., 20 hrs., 24 hrs., 48 hrs., 36 hrs., one week, or more).

With regard to production of an alcohol or aldehyde value added product of interest, the engineered microbes as described herein can be allowed to ferment under conditions that allow the microbe to convert glucose and xylose simultaneously into the desired alcohol or aldehyde product. In certain embodiments, the product is contemporaneously recovered and purified. For an aldehyde product, the aldehyde is preferably removed and recovered using well known gas stripping methods (e.g., sparging an inert gas through the culture medium), and subsequently purified using well known methods (e.g., condensation). Such methods are described in (e.g.) U.S. Pat. No. 9,708,631. Methods of recovering alcohol products are also known in the art, and include—by way of non-limiting examples—gas stripping, solvent extraction, and/or evaporation & condensation. See, e.g., US 2015/0225750.

Further Embodiments

Embodiment 1. A microbial cell comprising (1) a non-native xylose isomerase (xylA) gene; and (2) a non-native fructose-6-phosphate phosphoketolase (xfp) gene, and/or (3) a d-xylose ABC transporter (xylFGH).

Embodiment 2. The microbial cell of Embodiment 1, wherein the microbial cell further comprises: (4) a non-native xylulose kinase (xylB) gene.

Embodiment 3. The microbial cell of Embodiment 1 or 2, wherein the microbial cell is a eukaryote or a prokaryote.

Embodiment 4. The microbial cell of Embodiment 3, wherein the eukaryote is a yeast, or wherein the eukaryote belongs to a genus selected from the group consisting of *Saccharomyces, Pichia, Candida*, and *Aspergillus*.

Embodiment 5. The microbial cell of Embodiment 3, wherein the prokaryote belongs to a genus selected from the group consisting of *Escherichia, Bacillus, Corynebacterium, Alcaligenus, Zymomonas, Clostridium, Lactobacillus, Synechococcus*, and *Synechocystis*, and wherein the prokaryote is preferably *Escherichia coli*.

Embodiment 6. The microbial cell of any one of the previous embodiments, wherein the xylA gene comprises a coding sequence that is a native sequence, located on the chromosome, and the promoter driving the xylA is heterologous to the xylA coding sequence.

Embodiment 7. The microbial cell of any one of the previous embodiments, wherein the xfp gene comprises a nucleotide sequence that encodes a protein with at least 85% sequence identity to SEQ ID NO:1 or SEQ ID NO:2, preferably wherein the encoding nucleotide sequence is SEQ ID NO:3 or SEQ ID NO:4.

Embodiment 8. The microbial cell of any one of the previous embodiments, wherein the xylFGH gene comprises a nucleotide sequence that encodes a protein with at least 85% sequence identity to SEQ ID NOs:5, 6, & 7.

Embodiment 9. A method of improving xylose utilization in a microbial cell expressing xylose isomerase (xylA) and xylulose kinase (xylB) genes, the method comprising genetically modifying the microbial cell to overexpress a fructose-6-phosphate phosphoketolase (xfp) gene and/or a d-xylose ABC transporter (xylFGH) gene.

Embodiment 10. The method of Embodiment 9, wherein microbial cell is *Escherichia coli*.

Embodiment 11. The method of Embodiment 9 or 10, wherein the xylA and xylB are driven by a constitutive promoter.

Embodiment 12. The method of any one of Embodiments 9-11, wherein any one or more of the following is true: (a) the xylFGH gene comprises a nucleotide sequence that encodes a protein with at least 85% sequence identity to SEQ ID NOs:5, 6, & 7; and (b) the xfp gene comprises a nucleotide sequence encoding a protein with at least 85% identity to an amino acid sequence selected from the group consisting of SEQ ID NO:1 and SEQ ID NO:2, and preferably wherein the encoding nucleotide sequence is SEQ ID NO:3 or SEQ ID NO:4.

Embodiment 13. A method of producing an alcohol or aldehyde, the method comprising incubating the microbial cell of any one of Embodiments 1-8 in a feedstock comprising glucose and xylose, and preferably wherein the feedstock is corn stover or an extract of corn stover.

Embodiment 14. The method of Embodiment 13, wherein the aldehyde is selected from the group consisting of isobutryraldehyde, isobutyl alcohol, n-butyraldehyde, 3-methylbutyraldehyde, and methylbutyraldehyde, or wherein the alcohol is selected from the group consisting of ethanol, n-butanol, 3-methylbutanol and 2-methylbutanol.

EXAMPLES

Example 1

XylFGH strain construction. The xylA, xylB, xylF, xylG, and xylH genes were expressed from plasmid derivatives of pSA69 and pSA55, as described in Atsumi et al. (2008) *Nature* 451:86-89. The genes were amplified from genomic BW25113 DNA and then cloned into vectors as described in Gibson et al. (2009) *Nat. Methods* 6(5):343-45. Phusion DNA polymerase, Taq DNA ligase (New England Biolabs, Ipswich, Mass.), and T5 exonuclease (Epicentre, Madison, Wis.) were used for the assembly. Oligonucleotides were synthesized by Integrated DNA Technologies (Coralville, Iowa).

Figure 2:
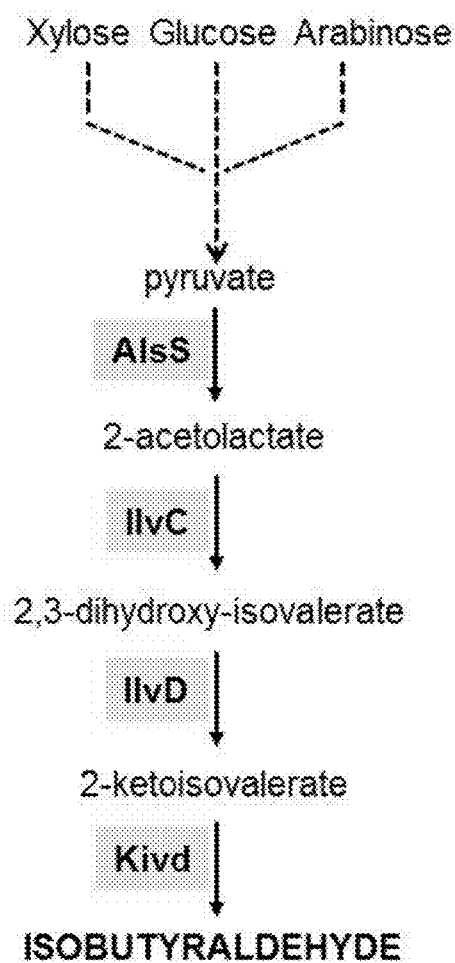
FIG. 2 depicts a metabolic pathway leading from glucose to isobutyraldehyde, and various enzymes involved in this and other pathways.

The BW25113 derivative of *E. coli* K-12 is available from the Coli Genetic Stock Center as CGSC #7636. Starting from CW25113, the following genes were knocked out by deletion mutations to produce strain 0E9: 1) yqhD; 2) ldhA; 3)frdBC; 4) adhE; 5) yjgB; and 6) yiaY. (See, FIG. 1). Each mutation was added individually using P1 transduction from the *E. coli* Keio collection. P1 transduction was conducted according to the method of Miller J H. *Experiments in Molecular Genetics*. Cold Spring Harbor Laboratory Press (31 Dec. 1972). The Keio collection is a library of single non-essential gene deletions in the BW25113 strain, and the preparation and results provided by the Keio collection is described by Baba et al., 2006, *Molecular Systems Biolog*, doi:10.1038/msb4100050. The knock-out pathways are illustrated in FIG. 2.

Starting from OE9, the INT5 strain was prepared by an alternate method, wherein single-gene knockouts were created using the λ red system described by Datsenko et al. (2000) PNAS 97(12):6640-45. In brief, Phage Red recombinase, which is synthesized under the control of an inducible promoter on an easily curable, low copy number plasmid, based on λ red recombinase targeted the *E. coli* chromosome genes to be disrupted with homologous PCR primers. The temperature sensitive pKD46 plasmid, that carries the λ red genes behind the araBAD promoter, was used.

Parent strains were transformed with pKD46. The pKD46 transformants were grown overnight at 30° C. in LB containing 100 μg/mL ampicillin. The next morning, the cells were diluted 1:100 into 20 mL of LB media containing 10 mM L-arabinose and ampicillin, and then grown at 30° C. Once cultures reached OD600=0.3-0.5, the cells were washed four times with 10% ice-cold glycerol and resuspended in 500 μL of 10% ice-cold glycerol. Aliquots of 50 μL were electroporated with 50-100 ng linear DNA PCR products of a kanamycin-sacB cassette with flanking 40-500 bp homologous regions of the target gene. Electroporated cells were recovered in 1 mL LB at 37° C. for 3-5 hours, and then plated on LB containing kanamycin (50 μg/mL) at 42° C. Integrants were identified by colony PCR. To remove the kanamycin-sacB cassette, a second integration was performed with a PCR product containing the target gene deletion flanked with 40-500 bp homologous regions.

Figure 3:
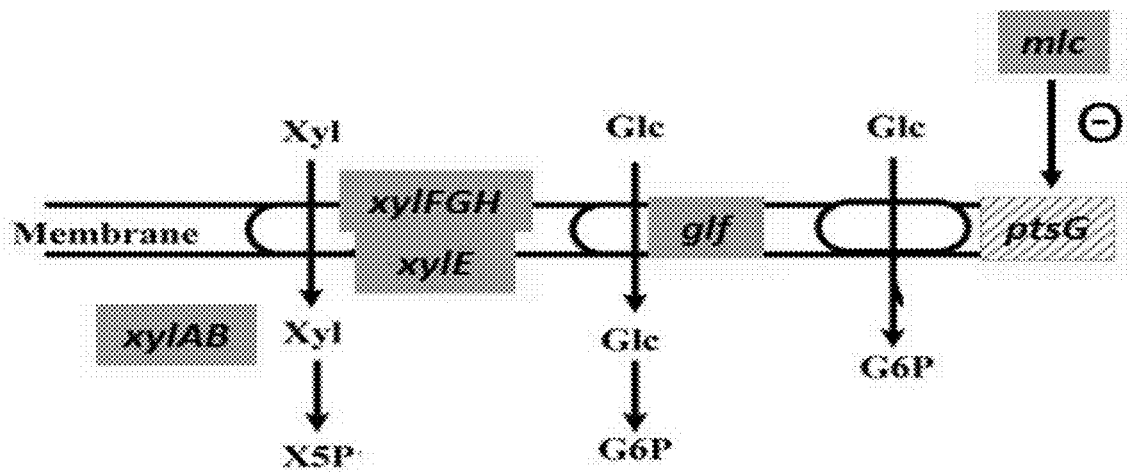
FIG. 3 depicts genetic modifications made in an exemplary *E. coli* strain.

INT5 incorporates (FIG. 3) the following features:

pta::PLlacO1-xylAB The pta gene (encoding phosphate acetyl-transferase) is ablated. With pta ablated cellular pyruvate is not used for aceetate production, but is available for producing isobutyraldehyde. A constitutive promoter (PLlacO1) was also inserted to drive overexpression of the xylAB operon.

adhE::PCP25-alsSilvCD The adhE gene (encoding aldehyde-alcohol dehydrogenase) was ablated. With adhE ablated, cellular pyruvate is not used for ethanol production, but is available for producing 2-ketoisovalerate. The PCP25 promoter was also inserted upstream of the alsS-lilvCD operon (AlsS catalyzes the conversion of pyruvate into 2-acetolactate, IlvC catalyzes the conversion of 2-acetolactate into 2,3-dihydro-isovalerate, and IlvD catalyzes the conversion of 2,3-dihydro-isovalerate into 2-ketoisovalerate).

yjgB::PCP25-kivd The yjgB gene (encoding an alcohol dehydrogenase) was ablated. With yjgB ablated, the isobutyraldehyde is not converted into isobutanol. The PCP25 promoter is also inserted upstream of the kivD gene. The kivD gene then catalyzes the conversion of 2-ketoisovalerate into isobutyraldehyde.

Example 2

Figure 4:
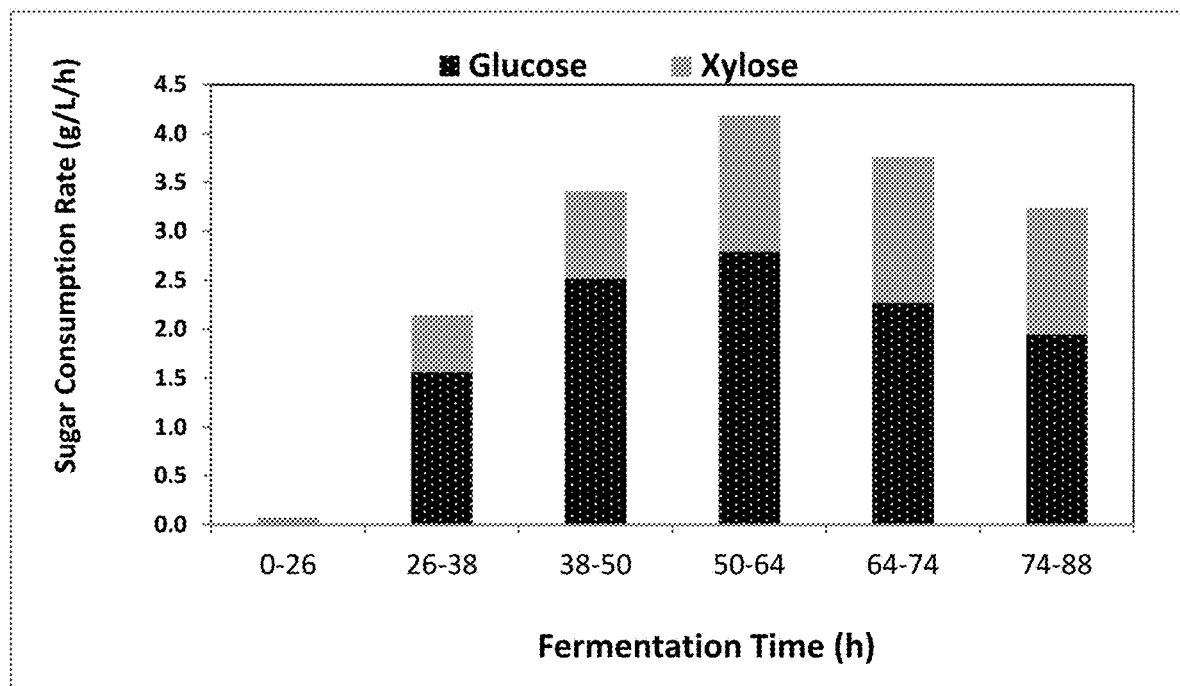
FIG. 4 depicts the quantity of glucose and xylose consumed over time by an exemplary, genetically modified *E. coli* strain overexpressing xylFGH.

Xylose utilization in the presence of glucose. E. coli strains as described above were grown overnight in LB with the appropriate antibiotics. The next morning, 40 μL of the overnight culture was subcultured into 2 mL of media containing the appropriate antibiotics with 4% (w/v) glucose and 2.43% (w/v) xylose. If necessary, IPTG was added at a concentration of 1 mM. After 24 hr. at 37° C., $OD_{600}$ was measured for each culture, and then the cells were pelleted at >20,000×g. The supernatant was transferred to a clean microcentrifuge tube. Dilutions of the supernatant were then used to measure glucose and xylose concentration using a glucose analyzer (YSI). The amount of glucose and xylose utilized was calculated by subtracting the final concentrations from the starting concentrations. As can be seen in FIG. 4, the strain expressing xylAB:xylFGH was fermenting both xylose and glucose after 50-64 hrs. post inoculation at a ratio of ~0.53 (grams xylose/grams glucose).

Example 3

Figure 5:
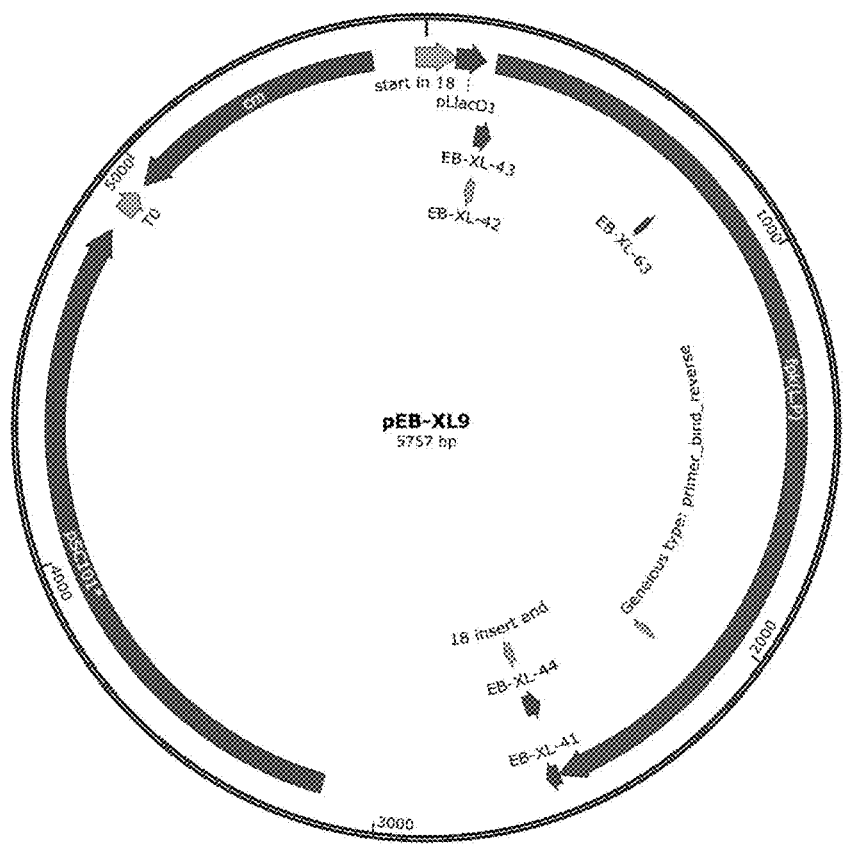
FIG. 5 depicts a plasmid map of pEB-XL-09.
Figure 6:
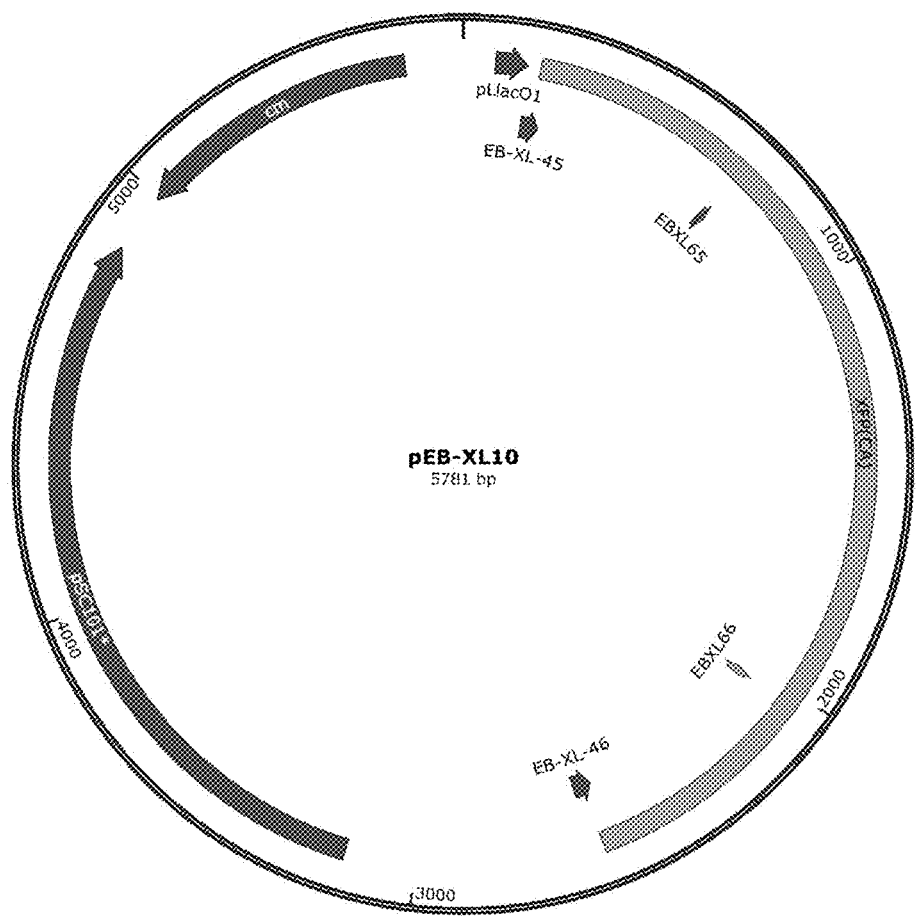
FIG. 6 depicts a plasmid map of pEB-XL-10.

Xfp strain construction. The xfp gene was cloned from C. acetobutylicum (FIG. 5, see Liu et al., 2012) and L. paraplantarum (FIG. 6, see Jeong et al., 2007), and assembled into a pEB plasmid backbone according to Gibson methods. In both cases, the xfp gene is under the control of PLlacO1 promoter. The rest of the elements on the plasmids are PSC101-replication origin and Chloramphenicol resistance gene.

As in Example 1 above, the xfp plasmids were transformed into the INT5 background. Single colonies were selected and cultured for test alongside an untransformed control.

Example 4

Figure 7:
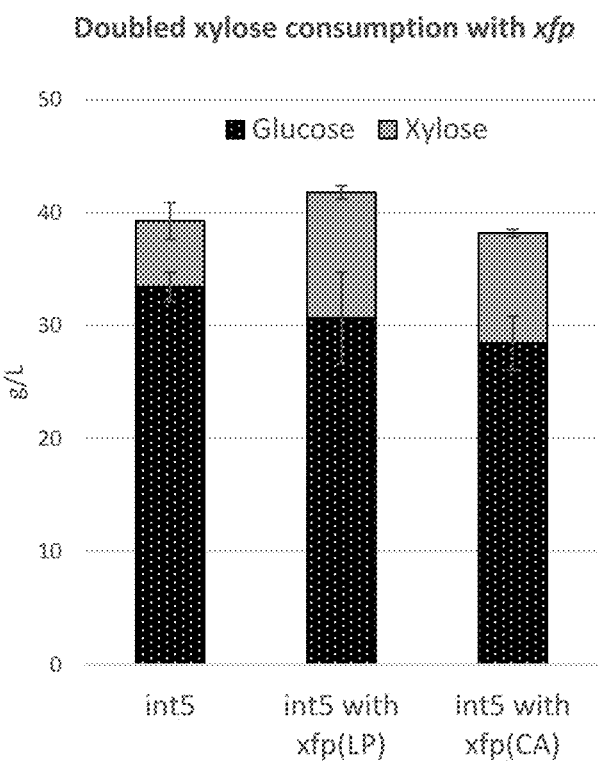
FIG. 7 shows xylose consumption in mixed glucose/xylose media by microbes expressing xfp.

Xylose utilization. In a 10 mL small scale test, 1% overnight cultures of the (transformants) from Example 3 were seeded into fresh medium starting with 35 g/L glucose and 18 g/L xylose. The cultures were incubated at 37° C. for 72 hours with shaking at 250 rpm. Cell cultured samples were collected at 0 and 72 hours. The supernatant of the culture samples were analyzed by HPLC for glucose, xylose, and acetate concentration. There were six replicates for each xfp overexpression strain, and four replicates for the negative control. FIG. 7 shows average xylose and glucose consumption for each strain tested. The L. paraplantarum Xfp resulted in acetate formation, but the C. acetobutylicum Xfp did not. As can be seen, both Xfp phosphoketolases enhanced xylose utilization in the mixed glucose/xylose medium relative to xylose utilization in the xylAB-overexpressing control strain.

It should be apparent to those skilled in the art that many more modifications besides those already described are possible without departing from the inventive concepts herein.

What is claimed is:

1. A microbial cell comprising (1) a non-native xylose isomerase (xylA) gene;
and (2) a non-native fructose-6-phosphate phosphoketolase (xfp) gene, and/or (3) a d-xylose ABC transporter (xylFGH).

2. The microbial cell of claim 1, wherein the microbial cell further comprises: (4) a non-native xylulose kinase (xylB) gene.

3. The microbial cell of claim 1, wherein the microbial cell is a eukaryote or a prokaryote.

4. The microbial cell of claim 3, wherein the eukaryote belongs to a genus selected from the group consisting of *Saccharomyces, Pichia, Candida*, and *Aspergillus*.

5. The microbial cell of claim 3, wherein the prokaryote belongs to a genus selected from the group consisting of *Escherichia, Bacillus, Corynebacterium, Alcaligenus, Zymomonas, Clostridium, Lactobacillus, Synechococcus*, and *Synechocystis*.

6. The microbial cell of claim 1, wherein the xylA gene comprises a coding sequence that is a native sequence, located on the chromosome, and the promoter driving the xylA is heterologous to the xylA coding sequence.

7. The microbial cell of claim 1, wherein the xfp gene comprises a nucleotide sequence that encodes a protein with at least 85% sequence identity to SEQ ID NO:1 or SEQ ID NO:2.

8. The microbial cell of claim 7, wherein the encoding nucleotide sequence is SEQ ID NO:3 or SEQ ID NO:4.

9. The microbial cell of claim 1, wherein the xylFGH gene comprises a nucleotide sequence that encodes a protein with at least 85% sequence identity to SEQ ID NO:5.

10. A method of producing an alcohol or aldehyde, the method comprising incubating the microbial cell of claim 1 in a feedstock comprising glucose and xylose, to produce an alcohol or aldehyde.

11. The method of claim 10, wherein the aldehyde is selected from the group consisting of isobutyraldehyde, isobutyl alcohol, n-butyraldehyde, 3-methylbutyraldehyde, and methylbutyraldehyde.

12. The method of claim 10, wherein the alcohol is selected from the group consisting of ethanol, n-butanol, 3-methylbutanol and 2-methylbutanol.

13. The method of claim 10, wherein the microbial cell further comprises: (3) a non-native xylB gene, and wherein the microbial cell is a eukaryote or a prokaryote.

14. The method of claim 10, wherein the xylA gene comprises a coding sequence that is a native sequence, located on the chromosome, and the promoter driving the xylA is heterologous to the xylA coding sequence.

15. The method of claim 10, wherein the xfp gene comprises a nucleotide sequence encoding a protein with at least 85% identity to an amino acid sequence selected from the group consisting of SEQ ID NO:1 and SEQ ID NO:2.

16. The method of claim 15, wherein the xfp nucleotide sequence is SEQ ID NO:3 or SEQ ID NO:4.

* * * * *

SEQUENCE LISTING

<160> NUMBER OF SEQ ID NOS: 10

<210> SEQ ID NO 1
<211> LENGTH: 796
<212> TYPE: PRT
<213> ORGANISM: Clostridium acetobutylicum

<400> SEQUENCE: 1

```
Met Gln Ser Ile Ile Gly Lys His Lys Asp Glu Gly Lys Ile Thr Pro
1               5                   10                  15

Glu Tyr Leu Lys Lys Ile Asp Ala Tyr Trp Arg Ala Ala Asn Phe Ile
            20                  25                  30

Ser Val Gly Gln Leu Tyr Leu Leu Asp Asn Pro Leu Leu Arg Glu Pro
        35                  40                  45

Leu Lys Pro Glu His Leu Lys Arg Lys Val Val Gly His Trp Gly Thr
    50                  55                  60

Ile Pro Gly Gln Asn Phe Ile Tyr Ala His Leu Asn Arg Val Ile Lys
65                  70                  75                  80
```

```
Lys Tyr Asp Leu Asp Met Ile Tyr Val Ser Gly Pro Gly His Gly Gly
                 85                  90                  95
Gln Val Met Val Ser Asn Ser Tyr Leu Asp Gly Thr Tyr Ser Glu Val
            100                 105                 110
Tyr Pro Asn Val Ser Arg Asp Leu Asn Gly Leu Lys Lys Leu Cys Lys
        115                 120                 125
Gln Phe Ser Phe Pro Gly Gly Ile Ser Ser His Met Ala Pro Glu Thr
    130                 135                 140
Pro Gly Ser Ile Asn Glu Gly Gly Glu Leu Gly Tyr Ser Leu Ala His
145                 150                 155                 160
Ser Phe Gly Ala Val Phe Asp Asn Pro Asp Leu Ile Thr Ala Cys Val
                165                 170                 175
Val Gly Asp Gly Glu Ala Glu Thr Gly Pro Leu Ala Thr Ser Trp Gln
            180                 185                 190
Ala Asn Lys Phe Leu Asn Pro Val Thr Asp Gly Ala Val Leu Pro Ile
        195                 200                 205
Leu His Leu Asn Gly Tyr Lys Ile Ser Asn Pro Thr Val Leu Ser Arg
    210                 215                 220
Ile Pro Lys Asp Glu Leu Glu Lys Phe Phe Glu Gly Asn Gly Trp Lys
225                 230                 235                 240
Pro Tyr Phe Val Glu Gly Glu Asp Pro Glu Ala Met His Lys Leu Met
                245                 250                 255
Ala Glu Thr Leu Asp Ile Val Thr Glu Glu Ile Leu Asn Ile Gln Lys
            260                 265                 270
Asn Ala Arg Glu Asn Asn Asp Cys Ser Arg Pro Lys Trp Pro Met Ile
        275                 280                 285
Val Leu Arg Thr Pro Lys Gly Trp Thr Gly Pro Lys Phe Val Asp Gly
    290                 295                 300
Val Pro Asn Glu Gly Ser Phe Arg Ala His Gln Val Pro Leu Ala Val
305                 310                 315                 320
Asp Arg Tyr His Thr Glu Asn Leu Asp Gln Leu Glu Glu Trp Leu Lys
                325                 330                 335
Ser Tyr Lys Pro Glu Glu Leu Phe Asp Glu Asn Tyr Arg Leu Ile Pro
            340                 345                 350
Glu Leu Glu Glu Leu Thr Pro Lys Gly Asn Lys Arg Met Ala Ala Asn
        355                 360                 365
Leu His Ala Asn Gly Gly Leu Leu Leu Arg Glu Leu Arg Thr Pro Asp
    370                 375                 380
Phe Arg Asp Tyr Ala Val Asp Val Pro Thr Pro Gly Ser Thr Val Lys
385                 390                 395                 400
Gln Asp Met Ile Glu Leu Gly Lys Tyr Val Arg Asp Val Val Lys Leu
                405                 410                 415
Asn Glu Asp Thr Arg Asn Phe Arg Ile Phe Gly Pro Asp Glu Thr Met
            420                 425                 430
Ser Asn Arg Leu Trp Ala Val Phe Glu Gly Thr Lys Arg Gln Trp Leu
        435                 440                 445
Ser Glu Ile Lys Glu Pro Asn Asp Glu Phe Leu Ser Asn Asp Gly Arg
    450                 455                 460
Ile Val Asp Ser Met Leu Ser Glu His Leu Cys Glu Gly Trp Leu Glu
465                 470                 475                 480
Gly Tyr Leu Leu Thr Gly Arg His Gly Phe Phe Ala Ser Tyr Glu Ala
                485                 490                 495
```

```
Phe Leu Arg Ile Val Asp Ser Met Ile Thr Gln His Gly Lys Trp Leu
            500                 505                 510

Lys Val Thr Ser Gln Leu Pro Trp Arg Lys Asp Ile Ala Ser Leu Asn
        515                 520                 525

Leu Ile Ala Thr Ser Asn Val Trp Gln Gln Asp His Asn Gly Tyr Thr
    530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
            580                 585                 590

Ser Lys His Pro Arg Gln Gln Trp Leu Thr Met Asp Gln Ala Val Lys
        595                 600                 605

His Val Glu Gln Gly Ile Ser Ile Trp Asp Trp Ala Ser Asn Asp Lys
    610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
            660                 665                 670

Glu Asn Glu His Pro His Gly Leu Ser Asp Lys Asp Tyr Asn Ala Leu
        675                 680                 685

Phe Thr Thr Asp Lys Pro Val Ile Phe Ala Phe His Gly Phe Ala His
    690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
            740                 745                 750

Asn Leu Pro Gln Leu Gly Asn Arg Gly Ala His Leu Val Gln Leu Met
        755                 760                 765

Asn Asp Lys Leu Val Glu His Asn Gln Tyr Ile Arg Glu Val Gly Glu
    770                 775                 780

Asp Leu Pro Glu Ile Thr Asn Trp Gln Trp His Val
785                 790                 795

<210> SEQ ID NO 2
<211> LENGTH: 796
<212> TYPE: PRT
<213> ORGANISM: Lactobacillus plantarum

<400> SEQUENCE: 2

Met Ser Glu Ala Ile Lys Ser Lys Thr Val Asp Tyr Ser Ser Asp Glu
1               5                   10                  15

Tyr Leu Lys Arg Val Asp Glu Tyr Trp Arg Ala Ala Asn Tyr Ile Ser
            20                  25                  30

Val Gly Gln Leu Tyr Leu Leu Asn Asn Pro Leu Leu Arg Glu Pro Leu
        35                  40                  45

Lys Ala Thr Asp Val Lys Val His Pro Ile Gly His Trp Gly Thr Ile
    50                  55                  60

Ala Gly Gln Asn Phe Ile Tyr Ala His Leu Asn Arg Ala Ile Asn Lys
65                  70                  75                  80
```

-continued

Tyr Gly Leu Asn Met Phe Tyr Ile Glu Gly Pro Gly His Gly Gly Gln
                 85                  90                  95

Val Met Val Ser Asn Ser Tyr Leu Asp Gly Thr Tyr Thr Glu Thr Tyr
            100                 105                 110

Pro Lys Ile Thr Gln Asp Lys Ala Gly Met Lys Arg Leu Phe Lys Gln
            115                 120                 125

Phe Ser Phe Pro Gly Gly Val Ala Ser His Ala Asp Pro Lys Thr Pro
            130                 135                 140

Gly Ser Ile His Glu Gly Glu Leu Gly Tyr Ser Ile Leu His Gly
145                 150                 155                 160

Ala Gly Ala Val Leu Asp Asn Pro Gly Leu Ile Ala Ala Thr Val Val
            165                 170                 175

Gly Asp Gly Glu Ser Glu Thr Gly Pro Leu Ala Thr Ser Trp Gln Val
            180                 185                 190

Asn Lys Phe Leu Asn Pro Ile Thr Asp Gly Thr Val Leu Pro Ile Leu
            195                 200                 205

Asn Leu Asn Gly Phe Lys Ile Ser Asn Pro Thr Val Leu Ser Arg Glu
            210                 215                 220

Ser His Glu Glu Leu Glu Asp Tyr Phe Lys Gly Leu Gly Trp Asp Pro
225                 230                 235                 240

His Phe Val Glu Gly Thr Asp Pro Ala Lys Met His Lys Ile Met Ala
                245                 250                 255

Glu Glu Leu Asp Lys Val Ile Glu Ile His Ala Ile Arg Lys Asn
                260                 265                 270

Ala Lys Asp Asn Asn Asp Glu Ser Arg Pro Lys Trp Pro Met Ile Val
            275                 280                 285

Phe Arg Ala Pro Lys Gly Trp Thr Gly Pro Lys Ser Trp Asp Gly Glu
            290                 295                 300

Pro Ile Glu Gly Ser Phe Arg Ala His Gln Ile Pro Ile Pro Val Asp
305                 310                 315                 320

Arg Asn His Met Glu His Ala Asp Lys Leu Val Asp Trp Leu Lys Ser
                325                 330                 335

Tyr Lys Pro Glu Glu Leu Phe Asp Glu Asn Gly Thr Leu Lys Pro Glu
            340                 345                 350

Ile Ala Ala Ile Ile Pro Glu Gly Gln Ala Arg Met Ala Ala Asn Pro
            355                 360                 365

Val Thr Asn Gly Gly Lys Leu Thr Lys Asp Leu Ile Thr Pro Asn Ile
            370                 375                 380

Asp Asp Tyr Ala Leu Asp Asn Lys Asp His Gly Lys Glu Asp Gly Ser
385                 390                 395                 400

Asp Met Thr Glu Leu Gly Lys Tyr Ile Arg Asp Leu Ile Glu Leu Asn
                405                 410                 415

Lys Asp Asn Lys Asn Phe Arg Gly Trp Gly Pro Asp Glu Thr Leu Ser
            420                 425                 430

Asn Lys Leu Gly Ala Ala Phe Glu Asp Thr Lys Arg Gln Trp Met Glu
            435                 440                 445

Pro Ile His Glu Pro Asn Asp Ala Leu Leu Ala Pro Gln Gly Arg Ile
            450                 455                 460

Ile Asp Ser Met Leu Ser Glu His Met Asp Glu Gly Met Leu Glu Ala
465                 470                 475                 480

Tyr Asn Leu Thr Gly Arg Tyr Gly Phe Phe Ala Ser Tyr Glu Ser Phe
                485                 490                 495

```
Leu Arg Val Val Asp Ser Met Leu Thr Gln His Phe Lys Trp Leu Arg
            500                 505                 510

Asn Ser His Glu Glu Thr Pro Trp Arg Ala Asp Val Pro Ser Leu Asn
        515                 520                 525

Val Ile Ala Ser Ser Thr Ala Phe Gln Gln Asp His Asn Gly Tyr Ser
    530                 535                 540

His Gln Asp Pro Gly Ile Ile Ser His Leu Ala Glu Lys Lys Thr Glu
545                 550                 555                 560

Tyr Val Arg Ala Tyr Leu Pro Gly Asp Ala Asn Thr Leu Ile Ala Thr
                565                 570                 575

Phe Asp Lys Ala Ile Gln Ser Lys Gln Leu Ile Asn Leu Ile Ile Ala
            580                 585                 590

Ser Lys His Pro Arg Pro Gln Trp Phe Thr Met Asp Glu Ala Lys Arg
        595                 600                 605

Leu Val Arg Asp Gly Leu Gly Val Asp Trp Ala Ser Thr Asp His
    610                 615                 620

Gly Glu Glu Pro Asp Val Val Phe Ala Thr Ala Gly Ser Glu Pro Thr
625                 630                 635                 640

Thr Glu Ser Leu Ala Ala Val Ser Ile Leu His Ala Arg Phe Pro Glu
                645                 650                 655

Met Lys Ile Arg Phe Ile Asn Val Val Asp Leu Leu Lys Leu Lys Lys
            660                 665                 670

Asp Asp Pro Arg Gly Leu Ser Asp Ala Glu Phe Asp Ala Phe Phe Thr
        675                 680                 685

Lys Asp Lys Pro Val Ile Phe Ala Tyr His Ala Tyr Asp Asp Leu Val
    690                 695                 700

Lys Thr Ser Phe Phe Asp Arg His Asn His Asn Leu His Val His Gly
705                 710                 715                 720

Tyr Arg Glu Glu Gly Asp Ile Thr Thr Pro Phe Asp Met Arg Val Arg
                725                 730                 735

Asn Glu Leu Asp Arg Phe His Leu Val Lys Ala Ala Leu Leu Ala Thr
            740                 745                 750

Pro Ala Tyr Ala Glu Lys Gly Ala His Val Ile Gln Glu Met Asn Ser
        755                 760                 765

Ile Leu Asp Lys His His Asp Tyr Ile Arg Ala Glu Gly Thr Asp Ile
    770                 775                 780

Pro Glu Val Glu Asn Trp Lys Trp Thr Ala Leu Lys
785                 790                 795

<210> SEQ ID NO 3
<211> LENGTH: 2391
<212> TYPE: DNA
<213> ORGANISM: Clostridium acetobutylicum

<400> SEQUENCE: 3
atgcaaagta taataggaaa acataaggat gaaggaaaaa tcacaccgga gtatctaaag      60
aaaattgatg catattggcg tgcagctaat tttatatctg taggtcaatt gtatttgcta     120
gacaatccat tgcttagaga acctttaaaa ccagaacatc taaaaagaaa agttgttggt     180
cactggggta ctattcctgg tcaaaacttt atttatgctc atcttaatcg tgttattaaa     240
aaatatgatt tagatatgat ttatgtttct ggtccaggtc atggtggaca agtaatggtg     300
tccaattctt atctagatgg aacctatagt gaagtttatc aaatgttag tcgtgatttg     360 aatggcttaa aaaagctatg taaacaattc tcttttccag gtggaatttc tagccatatg     420
```

-continued

| | |
|---|---|
| gctcctgaaa caccgggttc aataaatgaa gggggagaac taggctattc tttagcacat | 480 |
| tcttttggtg ctgtctttga taaccctgat ttgattactg cttgtgttgt tggagacgga | 540 |
| gaggcagaaa caggacctct tgcaacatct tggcaagcaa ataaattttt aaatccagtt | 600 |
| actgatggag cagtgcttcc tattttacat ttaaatggat acaaaattag taatcctact | 660 |
| gtgttgtctc gtattcctaa ggatgaactt gagaaattct ttgaaggaaa cggatggaag | 720 |
| ccttattttg tagaaggtga agatcctgaa gcaatgcata aattaatggc agaaacatta | 780 |
| gatatagtaa cagaagaaat tcttaatatt cagaaaaatg ctcgtgaaaa taacgattgt | 840 |
| tcacgaccaa agtggccaat gattgtattg cgtacaccaa agggatggac aggtccaaaa | 900 |
| tttgtagatg gtgttccaaa tgaaggatct ttccgtgcac accaagtacc acttgcagta | 960 |
| gatagatatc atacagaaaa cttagatcaa ttagaagagt ggcttaagag ttataaacca | 1020 |
| gaagaattat ttgacgaaaa ctatagacta ataccggaac ttgaagaatt aactccaaag | 1080 |
| ggaaataaga gaatgcggc taatttgcat gctaatggtg gtttattatt acgtgaacta | 1140 |
| cgtacacctg attttcgtga ttatgctgta gatgttccta ctccaggaag cacagttaag | 1200 |
| caggatatga ttgaacttgg aaaatatgtg cgtgatgttg ttaaattaaa cgaagatact | 1260 |
| cgtaatttcc gtattttggg accggatgaa actatgtcta atagattatg ggcagttttt | 1320 |
| gaaggaacga aacgtcaatg gttatcagaa attaagagc caaatgatga attcttatcg | 1380 |
| aatgatggac gtattgttga ttcaatgcta agcgaacatt tatgtgaagg ttggttagaa | 1440 |
| ggttatcttt taacaggacg tcatggtttc tttgcaagtt atgaagcctt ccttcgtatt | 1500 |
| gttgattcta tgattactca gcatggtaag tggttaaagg taacatcaca gctaccatgg | 1560 |
| agaaaagata ttgcttcttt aaatttaata gcaacatcta atgtatggca gcaggatcat | 1620 |
| aatgatata ctcatcaaga tccaggttta ttaggacata ttgtggataa aaaacctgaa | 1680 |
| atagttagag catatttacc agcagatgcc aataccttat tagccgtatt tgataaatgc | 1740 |
| cttcatacta aacacaagat taatttatta gtaacatcaa aacatccaag acaacagtgg | 1800 |
| ttaacaatgg atcaagcagt taagcatgta gagcaaggaa taagcatttg ggattgggca | 1860 |
| agtaatgaca aaggacaaga acctgatgta gttatagctt cctgtggaga tactccaaca | 1920 |
| ttagaggctt tggcagctgt tacaatcctt catgaacatt taccagaatt aaaagttcgt | 1980 |
| tttgtaaatg tagtggatat gatgaaatta ttacctgaaa atgagcatcc tcatggctta | 2040 |
| agcgataagg attataatgc cttatttaca acagataagc ctgtaatatt tgcattccat | 2100 |
| ggatttgcac atttaataaa tcaattaaca tatcatcgtg aaaatagaaa tttacatgta | 2160 |
| catggttata tggaagaggg aactattaca acaccatttg atatgcgtgt tcaaaataaa | 2220 |
| ttagatcgtt ttaatcttgt aaaagatgta gtagagaatt taccctcagct tggaaatcgt | 2280 |
| ggagcacatc ttgttcagtt aatgaatgat aaattagtag aacataacca atacattcgt | 2340 |
| gaggttggag aagatttgcc agaaataact aattggcagt ggcatgtata a | 2391 |

<210> SEQ ID NO 4
<211> LENGTH: 2391
<212> TYPE: DNA
<213> ORGANISM: Lactobacillus plantarum

<400> SEQUENCE: 4

| | |
|---|---|
| atgagtgaag caattaaatc caaaacagtt gattactctt ctgatgaata tctaaaacgc | 60 |
| gttgatgaat attggcgtgc tgctaactac atctcagttg gtcaactcta tctactaaat | 120 |
| aacccgttac ttcgggaacc actaaaggcg accgacgtga agttcatcc aatcggccat | 180 |

```
tggggcacga ttgctggtca aaactttatt tatgcccatt taaaccgggc aatcaataag      240
tatggcttga acatgttcta cattgaaggc cctggtcatg gtggtcaagt aatggtttct      300
aactccctact tagatggcac ctatacggaa acgtatccta aaatcaccca agacaaagct     360
gggatgaaac gcttattcaa gcaattctca ttcccaggcg gggttgcttc ccatgccgat      420
cctaagacgc ctggttcgat ccatgaaggt ggcgaacttg gctactcaat cctgcatggt     480
gctggtgcag tattagataa tccaggttta attgccgcta ccgttgttgg tgatggtgaa      540
tctgaaactg gccattggc aacttcttgg caagttaaca agttccttaa cccaattaca       600
gacgggacag tcttaccaat cttgaactta acggcttca agatttctaa tccaacagtt      660
ctttcacgtg aatcacatga agaacttgaa gactacttta aaggtctagg ctgggatcca     720
cactttgttg aaggtacaga ccctgccaag atgcacaaaa tcatggctga agaattggat      780
aaagtcattg aagaaatcca cgcaattcgt aagaacgcca aggataacaa tgatgaatct     840
cgtcctaagt ggccaatgat tgttttccgg gcacctaagg gctggaccgg tcctaagagt     900
tgggacggcg aaccaattga aggttcattc cgggctcacc aaattccaat tcctgtcgat     960
cgcaatcaca tggaacacgc cgacaaatta gttgactggc tcaaatcata caaaccagaa   1020
gaattatttg atgaaaatgg tacttttaaaa ccagaaattg ccgcaatcat ccctgaaggc  1080
caagctcgta tggctgctaa ccccgtcact aacggcggta agttaactaa agacttaatt    1140
acaccaaata tcgatgatta tgcttttgga caacaaggatc acggtaagga agacggttca  1200
gacatgactg aacttggtaa gtatatccgt gatttaattg agttgaacaa agacaacaag    1260
aacttccgtg gctggggtcc tgacgaaaacc ttatctaaca aactaggcgc tgcttttgaa  1320
gataccaaac gtcagtggat ggaaccaatc cacgaaccta atgatgcttt gttagcacct   1380
caaggccgga ttattgactc catgttgtca gaacacatgg atgaagggat gttggaagct   1440
tacaatttaa ccggacgtta cggtttcttc gcaagttatg aatcattcct gcgcgttgtg    1500
gattcaatgt taacccaaca cttcaagtgg ttacggaatt ctcacgaaga aaccccttgg   1560
cgggctgatg taccttcact gaatgtgatt gcatcatcaa cagccttcca acaagatcac   1620
aatggttact ctcaccaaga tccaggtatc atttcacact ggctgaaaaa gaagaccgaa  1680
tacgttcgtg cctatcttcc aggtgatgcc aatactttga ttgcaacctt tgataaggct    1740
atccaaagca aacaattgat taatttaatc attgccagca agcaccctcg tccacaatgg   1800
ttcacaatgg acgaagctaa gcgcttagtt cgtgatggcc ttggtgttgt tgattgggca    1860
agcactgatc atggtgaaga acccgacgtt gtcttcgcaa ctgccggctc tgaaccaacg   1920
actgaaagct agctgccgt atcaatcttg catgcacgct tccctgaaat gaagattcgc    1980
ttcattaacg ttgttgatct tctgaagctg aagaaagacg accctcgtgg tttatcagat   2040
gctgaattg atgctttctt cactaaggac aaaccagtta tctttgctta tcatgcatac    2100
gacgacttag taaagaccag cttcttcgat cgccataacc ataacttaca cgttcatggt   2160
taccgcgaag aaggcgacat tacaacgcca ttcgacatgc gtgttcgcaa cgaactcgat   2220
cgtttccact tagtcaaagc tgccttatta gcaacgccag cttatgccga aaaggtgcc    2280
catgtcattc aagagatgaa cagcatttta gacaagcatc atgactatat ccgtgctgaa   2340
ggtaccgata ttccagaagt tgaaaactgg aaatggactg cattgaagta g            2391
```

<210> SEQ ID NO 5
<211> LENGTH: 330
<212> TYPE: PRT
<213> ORGANISM: Escherichia coli

<400> SEQUENCE: 5

Met Lys Ile Lys Asn Ile Leu Leu Thr Leu Cys Thr Ser Leu Leu Leu
1               5                   10                  15

Thr Asn Val Ala Ala His Ala Lys Glu Val Lys Ile Gly Met Ala Ile
            20                  25                  30

Asp Asp Leu Arg Leu Glu Arg Trp Gln Lys Asp Arg Asp Ile Phe Val
        35                  40                  45

Lys Lys Ala Glu Ser Leu Gly Ala Lys Val Phe Val Gln Ser Ala Asn
    50                  55                  60

Gly Asn Glu Glu Thr Gln Met Ser Gln Ile Glu Asn Met Ile Asn Arg
65                  70                  75                  80

Gly Val Asp Val Leu Val Ile Ile Pro Tyr Asn Gly Gln Val Leu Ser
                85                  90                  95

Asn Val Val Lys Glu Ala Lys Gln Glu Gly Ile Lys Val Leu Ala Tyr
            100                 105                 110

Asp Arg Met Ile Asn Asp Ala Asp Ile Asp Phe Tyr Ile Ser Phe Asp
        115                 120                 125

Asn Glu Lys Val Gly Glu Leu Gln Ala Lys Ala Leu Val Asp Ile Val
    130                 135                 140

Pro Gln Gly Asn Tyr Phe Leu Met Gly Gly Ser Pro Val Asp Asn Asn
145                 150                 155                 160

Ala Lys Leu Phe Arg Ala Gly Gln Met Lys Val Leu Lys Pro Tyr Val
                165                 170                 175

Asp Ser Gly Lys Ile Lys Val Val Gly Asp Gln Trp Val Asp Gly Trp
            180                 185                 190

Leu Pro Glu Asn Ala Leu Lys Ile Met Glu Asn Ala Leu Thr Ala Asn
        195                 200                 205

Asn Asn Lys Ile Asp Ala Val Val Ala Ser Asn Asp Ala Thr Ala Gly
    210                 215                 220

Gly Ala Ile Gln Ala Leu Ser Ala Gln Gly Leu Ser Gly Lys Val Ala
225                 230                 235                 240

Ile Ser Gly Gln Asp Ala Asp Leu Ala Gly Ile Lys Arg Ile Ala Ala
                245                 250                 255

Gly Thr Gln Thr Met Thr Val Tyr Lys Pro Ile Thr Leu Leu Ala Asn
            260                 265                 270

Thr Ala Ala Glu Ile Ala Val Glu Leu Gly Asn Gly Gln Glu Pro Lys
        275                 280                 285

Ala Asp Thr Thr Leu Asn Asn Gly Leu Lys Asp Val Pro Ser Arg Leu
    290                 295                 300

Leu Thr Pro Ile Asp Val Asn Lys Asn Ile Lys Asp Thr Val Ile
305                 310                 315                 320

Lys Asp Gly Phe His Lys Glu Ser Glu Leu
                325                 330

<210> SEQ ID NO 6
<211> LENGTH: 513
<212> TYPE: PRT
<213> ORGANISM: Escherichia coli

<400> SEQUENCE: 6

Met Pro Tyr Leu Leu Glu Met Lys Asn Ile Thr Lys Thr Phe Gly Ser
1               5                   10                  15

Val Lys Ala Ile Asp Asn Val Cys Leu Arg Leu Asn Ala Gly Glu Ile
            20                  25                  30

```
Val Ser Leu Cys Gly Glu Asn Gly Ser Gly Lys Ser Thr Leu Met Lys
         35                  40                  45
Val Leu Cys Gly Ile Tyr Pro His Gly Ser Tyr Glu Gly Glu Ile Ile
 50                  55                  60
Phe Ala Gly Glu Glu Ile Gln Ala Ser His Ile Arg Asp Thr Glu Arg
 65                  70                  75                  80
Lys Gly Ile Ala Ile Ile His Gln Glu Leu Ala Leu Val Lys Glu Leu
                 85                  90                  95
Thr Val Leu Glu Asn Ile Phe Leu Gly Asn Glu Ile Thr His Asn Gly
                100                 105                 110
Ile Met Asp Tyr Asp Leu Met Thr Leu Arg Cys Gln Lys Leu Leu Ala
             115                 120                 125
Gln Val Ser Leu Ser Ile Ser Pro Asp Thr Arg Val Gly Asp Leu Gly
         130                 135                 140
Leu Gly Gln Gln Gln Leu Val Glu Ile Ala Lys Ala Leu Asn Lys Gln
145                 150                 155                 160
Val Arg Leu Leu Ile Leu Asp Glu Pro Thr Ala Ser Leu Thr Glu Gln
                165                 170                 175
Glu Thr Ser Ile Leu Leu Asp Ile Ile Arg Asp Leu Gln Gln His Gly
            180                 185                 190
Ile Ala Cys Ile Tyr Ile Ser His Lys Leu Asn Glu Val Lys Ala Ile
        195                 200                 205
Ser Asp Thr Ile Cys Val Ile Arg Asp Gly Gln His Ile Gly Thr Arg
    210                 215                 220
Asp Ala Ala Gly Met Ser Glu Asp Asp Ile Ile Thr Met Met Val Gly
225                 230                 235                 240
Arg Glu Leu Thr Ala Leu Tyr Pro Asn Glu Pro His Thr Thr Gly Asp
                245                 250                 255
Glu Ile Leu Arg Ile Glu His Leu Thr Ala Trp His Pro Val Asn Arg
            260                 265                 270
His Ile Lys Arg Val Asn Asp Val Ser Phe Ser Leu Lys Arg Gly Glu
        275                 280                 285
Ile Leu Gly Ile Ala Gly Leu Val Gly Ala Gly Arg Thr Glu Thr Ile
    290                 295                 300
Gln Cys Leu Phe Gly Val Trp Pro Gly Gln Trp Glu Gly Lys Ile Tyr
305                 310                 315                 320
Ile Asp Gly Lys Gln Val Asp Ile Arg Asn Cys Gln Gln Ala Ile Ala
                325                 330                 335
Gln Gly Ile Ala Met Val Pro Glu Asp Arg Lys Arg Asp Gly Ile Val
            340                 345                 350
Pro Val Met Ala Val Gly Lys Asn Ile Thr Leu Ala Ala Leu Asn Lys
        355                 360                 365
Phe Thr Gly Gly Ile Ser Gln Leu Asp Asp Ala Ala Glu Gln Lys Cys
    370                 375                 380
Ile Leu Glu Ser Ile Gln Gln Leu Lys Val Lys Thr Ser Ser Pro Asp
385                 390                 395                 400
Leu Ala Ile Gly Arg Leu Ser Gly Gly Asn Gln Gln Lys Ala Ile Leu
                405                 410                 415
Ala Arg Cys Leu Leu Leu Asn Pro Arg Ile Leu Ile Leu Asp Glu Pro
            420                 425                 430
Thr Arg Gly Ile Asp Ile Gly Ala Lys Tyr Glu Ile Tyr Lys Leu Ile
        435                 440                 445
```

```
Asn Gln Leu Val Gln Gln Gly Ile Ala Val Ile Val Ile Ser Ser Glu
    450                 455                 460

Leu Pro Glu Val Leu Gly Leu Ser Asp Arg Val Leu Val Met His Glu
465                 470                 475                 480

Gly Lys Leu Lys Ala Asn Leu Ile Asn His Asn Leu Thr Gln Glu Gln
                485                 490                 495

Val Met Glu Ala Ala Leu Arg Ser Glu His His Val Glu Lys Gln Ser
                500                 505                 510

Val

<210> SEQ ID NO 7
<211> LENGTH: 393
<212> TYPE: PRT
<213> ORGANISM: Escherichia coli

<400> SEQUENCE: 7

Met Ser Lys Ser Asn Pro Ser Glu Val Lys Leu Ala Val Pro Thr Ser
1               5                   10                  15

Gly Gly Phe Ser Gly Leu Lys Ser Leu Asn Leu Gln Val Phe Val Met
                20                  25                  30

Ile Ala Ala Ile Ile Ala Ile Met Leu Phe Phe Thr Trp Thr Thr Asp
            35                  40                  45

Gly Ala Tyr Leu Ser Ala Arg Asn Val Ser Asn Leu Leu Arg Gln Thr
    50                  55                  60

Ala Ile Thr Gly Ile Leu Ala Val Gly Met Val Phe Val Ile Ile Ser
65                  70                  75                  80

Ala Glu Ile Asp Leu Ser Val Gly Ser Met Met Gly Leu Leu Gly Gly
                85                  90                  95

Val Ala Ala Ile Cys Asp Val Trp Leu Gly Trp Pro Leu Pro Leu Thr
            100                 105                 110

Ile Ile Val Thr Leu Val Leu Gly Leu Leu Gly Ala Trp Asn Gly
        115                 120                 125

Trp Trp Val Ala Tyr Arg Lys Val Pro Ser Phe Ile Val Thr Leu Ala
    130                 135                 140

Gly Met Leu Ala Phe Arg Gly Ile Leu Ile Gly Ile Thr Asn Gly Thr
145                 150                 155                 160

Thr Val Ser Pro Thr Ser Ala Ala Met Ser Gln Ile Gly Gln Ser Tyr
                165                 170                 175

Leu Pro Ala Ser Thr Gly Phe Ile Ile Gly Ala Leu Gly Leu Met Ala
            180                 185                 190

Phe Val Gly Trp Gln Trp Arg Gly Arg Met Arg Arg Gln Ala Leu Gly
        195                 200                 205

Leu Gln Ser Pro Ala Ser Thr Ala Val Val Gly Arg Gln Ala Leu Thr
    210                 215                 220

Ala Ile Ile Val Leu Gly Ala Ile Trp Leu Leu Asn Asp Tyr Arg Gly
225                 230                 235                 240

Val Pro Thr Pro Val Leu Leu Thr Leu Leu Leu Gly Gly Met
                245                 250                 255

Phe Met Ala Thr Arg Thr Ala Phe Gly Arg Arg Ile Tyr Ala Ile Gly
            260                 265                 270

Gly Asn Leu Glu Ala Ala Arg Leu Ser Gly Ile Asn Val Glu Arg Thr
        275                 280                 285

Lys Leu Ala Val Phe Ala Ile Asn Gly Leu Met Val Ala Ile Ala Gly
    290                 295                 300
```

```
Leu Ile Leu Ser Ser Arg Leu Gly Ala Gly Ser Pro Ser Ala Gly Asn
305                 310                 315                 320

Ile Ala Glu Leu Asp Ala Ile Ala Ala Cys Val Ile Gly Gly Thr Ser
                325                 330                 335

Leu Ala Gly Gly Val Gly Ser Val Ala Gly Ala Val Met Gly Ala Phe
            340                 345                 350

Ile Met Ala Ser Leu Asp Asn Gly Met Ser Met Met Asp Val Pro Thr
        355                 360                 365

Phe Trp Gln Tyr Ile Val Lys Gly Ala Ile Leu Leu Leu Ala Val Trp
    370                 375                 380

Met Asp Ser Ala Thr Lys Arg Arg Ser
385                 390

<210> SEQ ID NO 8
<211> LENGTH: 993
<212> TYPE: DNA
<213> ORGANISM: Escherichia coli

<400> SEQUENCE: 8
atgaaaataa agaacattct actcacccct tgcacctcac tcctgcttac caacgttgct      60
gcacacgcca aagaagtcaa aataggtatg gcgattgatg atctccgtct tgaacgctgg     120
caaaaagatc gagatatctt tgtgaaaaag gcagaatctc tcggcgcgaa agtatttgta     180
cagtctgcaa atggcaatga agaaacacaa atgtcgcaga ttgaaaacat gataaaccgg     240
ggtgtcgatg ttcttgtcat tattccgtat aacggtcagg tattaagtaa cgttgtaaaa     300
gaagccaaac aagaaggcat taagtatta gcttacgacc gtatgattaa cgatgcggat     360
atcgattttt atatttcttt cgataacgaa aaagtcggtg aactgcaggc aaaagccctg     420
gtcgatattg ttccgcaagg taattacttc ctgatgggcg gctcgccggt agataacaac     480
gccaagctgt ccgcgccgg acaaatgaaa gtgttaaaac cttacgttga ttccggaaaa     540
attaaagtcg ttggtgacca atgggttgat ggctggttac cggaaaacgc attgaaaatt     600
atggaaaacg cgctaaccgc caataataac aaaattgatg ctgtagttgc ctcaaacgat     660
gccaccgcag gtgggcaat tcaggcatta agcgcgcaag gtttatcagg aaagtagca      720 atctccggcc aggatgcgga tctcgcaggt attaaacgta ttgctgccgg tacgcaaact     780
atgacggtgt ataaacctat tacgttgttg gcaaatactg ccgcagaaat tgccgttgag     840
ttgggcaatg gtcaggaacc aaaagcagat accacactga ataatggcct gaaagatgtc     900
ccctcccgcc tcctgacacc gatcgatgtg aataaaaaca acatcaaaga tacggtaatt     960
aaagacggat tccacaaaga gagcgagctg taa                                 993

<210> SEQ ID NO 9
<211> LENGTH: 1542
<212> TYPE: DNA
<213> ORGANISM: Escherichia coli

<400> SEQUENCE: 9
atgccttatc tacttgaaat gaagaacatt accaaaacct tcggcagtgt gaaggcgatt      60
gataacgtct gcttgcggtt gaatgctggc gaaatcgtct cactttgtgg ggaaaatggg     120
tctggtaaat caacgctgat gaaagtgctg tgtggtattt atcccatgg ctcctacgaa      180 ggcgaaatta tttttgcggg agaagagatt caggcgagtc acatccgcga taccgaacgc     240
aaaggtatcg ccatcattca tcaggaattg gccctggtga agaattgac cgtgctggaa      300 aatatcttcc tgggtaacga ataacccac aatggcatta tggattatga cctgatgacg     360
```

```
ctacgctgtc agaagctgct cgcacaggtc agtttatcca tttcacctga tacccgcgtt      420
ggcgatttag ggcttgggca acaacaactg gttgaaattg ccaaggcact aataaaacag      480
gtgcgcttgt taattctcga tgaaccgaca gcctcattaa ctgagcagga aacgtcgatt      540
ttactggata ttattcgcga tctacaacag cacggtatcg cctgtattta tatttcgcac      600
aaactcaacg aagtcaaagc gatttccgat acgatttgcg ttattcgcga cggacagcac      660
attggtacgc gtgatgctgc cggaatgagt gaagacgata ttatcaccat gatggtcggg      720
cgagagttaa ccgcgcttta ccctaatgaa ccacatacca ccggagatga atattacgt       780
attgaacatc tgacggcatg gcatccggtt aatcgtcata ttaaacgagt taatgatgtc      840
tcgttttccc tgaaacgtgg cgaaatattg gtattgccg gactcgttgg tgccggacgt       900
accgagacca ttcagtgcct gtttggtgtg tgggcccggac aatgggaagg aaaaatttat    960
attgatggca acaggtaga tattcgtaac tgtcagcaag ccatcgccca ggggattgcg       1020
atggtccccg aagacagaaa gcgcgacggc atcgttccgg taatggcggt tggtaaaaat     1080
attaccctcg ccgcactcaa taaatttacc ggtggcatta gccagcttga tgacgcggca     1140
gagcaaaaat gtattctgga atcaatccag caactcaaag ttaaaacgtc gtcccccgac      1200
cttgctattg gacgtttgag cggcggcaat cagcaaaaag cgatcctcgc tcgctgtctg     1260
ttacttaacc cgcgcattct cattcttgat gaacccacca ggggtatcga tattggcgcg     1320
aaatacgaga tctacaaatt aattaaccaa ctcgtccagc agggtattgc cgttattgtc     1380
atctcttccg aattacctga agtgctcggc cttagcgatc gtgtactggt gatgcatgaa     1440
gggaaactaa aagccaacct gataaatcat aacctgactc aggagcaggt gatggaagcc     1500
gcattgagga gcgaacatca tgtcgaaaag caatccgtct ga                        1542

<210> SEQ ID NO 10
<211> LENGTH: 1182
<212> TYPE: DNA
<213> ORGANISM: Escherichia coli

<400> SEQUENCE: 10
atgtcgaaaa gcaatccgtc tgaagtgaaa ttggccgtac cgacatccgg tggcttctcc       60
gggctgaaat cactgaattt gcaggtcttc gtgatgattg cagctatcat cgcaatcatg      120
ctgttcttta cctggaccac cgatggtgcc tacttaagcg cccgtaacgt ctccaacctg      180
ttacgccaga ccgcgattac cggcatcctc gcggtaggaa tggtgttcgt cataatttct      240
gctgaaatcg acctttccgt cggctcaatg atggggctgt taggtggcgt cgcggcgatt      300
tgtgacgtct ggttaggctg gcctttgcca cttaccatca ttgtgacgct ggttctggga      360
ctgcttctcg gtgcctggaa cggatggtgg gtcgcgtacc gtaaagtccc ttcatttatt      420
gtcaccctcg cgggcatgtt ggcatttcgc ggcatactca ttggcatcac caacggcacg      480
actgtatccc ccaccagcgc cgcgatgtca caaattgggc aaagctatct ccccgccagt      540
accggcttca tcattggcgc gcttggctta atggcttttg ttggttggca atggcgcgga      600
agaatgcgcc gtcaggcttt gggtttacag tctccggcct ctaccgcagt agtcggtcgc     660
caggctttaa ccgctatcat cgtattaggc gcaatctggc tgttgaatga ttaccgtggc     720
gttcccactc ctgttctgct gctgacgttg ctgttactcg gcggaatgtt tatggcaacg     780
cggacggcat ttggacgacg catttatgcc atcggcggca atctggaagc agcacgtctc      840
tccgggatta acgttgaacg caccaaactt gccgtgttcg cgattaacgg attaatggta     900
gccatcgccg gattaatcct tagttctcga cttggcgctg gttcaccttc tgcgggaaat     960
```

-continued

```
atcgccgaac tggacgcaat tgcagcatgc gtgattggcg gcaccagcct ggctggcggt    1020
gtgggaagcg ttgccggagc agtaatgggg gcatttatca tggcttcact ggataacggc    1080
atgagtatga tggatgtacc gaccttctgg cagtatatcg ttaaaggtgc gattctgttg    1140
ctggcagtat ggatggactc cgcaaccaaa cgccgttctt ga                       1182
```